(12) United States Patent
Taylor (10) Patent No.: US 9,210,847 B2
(45) Date of Patent: Dec. 15, 2015

(54) SOYBEAN VARIETIES AND METHODS FOR PRODUCING SAID VARIETIES

(75) Inventor: G. Robert Taylor, West Lafayette, IN (US)

(73) Assignee: Kenavis Corporation, LLC, West Lafayette, IN (US)

( * ) Notice: Subject to any disclaimer, the term of this patent is extended or adjusted under 35 U.S.C. 154(b) by 1223 days.

(21) Appl. No.: 13/102,591

(22) Filed: May 6, 2011

(65) Prior Publication Data

US 2012/0284873 A1    Nov. 8, 2012

(51) Int. Cl.
*A01H 5/10*    (2006.01)
*A01H 1/04*    (2006.01)
*A01H 4/00*    (2006.01)

(52) U.S. Cl.
CPC .. *A01H 4/00* (2013.01); *A01H 1/04* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 5,811,636 A | 9/1998 | Hanna et al. | |
| 7,541,514 B2 * | 6/2009 | Carman | 800/269 |
| 2005/0155111 A1 * | 7/2005 | Carman | 800/287 |
| 2007/0136895 A1 | 6/2007 | Siddiqi et al. | |

FOREIGN PATENT DOCUMENTS

| | | |
|---|---|---|
| WO | WO89-00810 | 2/1989 |
| WO | WO2006/009922 | 1/2006 |

OTHER PUBLICATIONS

Chen et al. Euphytica 36: 333-343 (1987).*
Chen et al. Theoretical and Applied Genetics 69: 271-277 (1985).*
Kenworthy et al., "Polyembryony is Soybeans," Crop Science, Nov. 1, 1973, vol. 13, pp. 637-639.
Vernon et al., "Embryonic Transformation of the Suspensor in Twin, a Polyembryonic Mutant of *Arabidopsis*," Developmental Biology, Jun. 8, 1994, vol. 165, pp. 566-573.
Chen et al., "The Frequency of Polyembryonic Seedlings and Polyploids from ms1 Soybean," Theoretical and Applied Genetics, May 3, 1984, vol. 69, pp. 271-277.
Graybosch et al., "Male Sterility in Soybean—An Overview," American Journal of Botany, Jan. 1, 1988, vol. 75, Iss. 1, pp. 144-156.
Shorter et al, "Multiple Seedling Development in Soybeans," The Journal of Heredity, Nov. 1, 1975, vol. 66, pp. 323-326.
Buchheim et al., "Maturation of Soybean Somatic Embryos and the Transition to Plantlet Growth," Plant Physiology, vol. 89, No. 3, Mar. 1, 1989, pp. 768-775.

* cited by examiner

*Primary Examiner* — David T Fox
(74) *Attorney, Agent, or Firm* — Barnes & Thornburg LLP (57) ABSTRACT

The present invention provides apomictic soybean varieties and methods of making the same.

20 Claims, 11 Drawing Sheets

SOYBEAN VARIETIES AND METHODS FOR PRODUCING SAID VARIETIES

BACKGROUND OF THE INVENTION

The present invention generally provides apomictic soybean varieties and more particularly, apomictic soybean varieties having a determinate growth habit, a percent conversion greater than 60% for conversion of flowers to pods and at least 100 pods per plant. The present invention further provides methods for producing apomictic soybean varieties comprising selecting double-ovule seeds, growing said seeds and then selecting for apomictic varieties.

There are numerous steps in the development of any novel, desirable plant germplasm. Plant breeding begins with the analysis and definition of problems and weaknesses of the current germplasm, the establishment of desired goals, and the definition of specific breeding objectives. The next step is selection of germplasm that possess the traits to meet the desired goals. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in compositional traits.

Reproduction in plants is ordinarily classified as sexual or asexual. The term apomixis is generally accepted as the replacement of sexual reproduction by various forms of asexual reproduction. Apomixis is a genetically controlled method of reproduction in plants where the embryo is formed without union of an egg and sperm nuclei. There are three basic types of apomictic reproduction: 1) apospory—embryo develops from a chromosomally unreduced egg in an embryo sac derived from the nucellus, 2) diplospory—embryo develops from an egg in an embryo sac derived from the unreduced megaspore mother cell, and 3) adventitious embryony—embryo develops directly from a somatic cell. In most forms of apomixis, pseudogamy or fertilization of the polar nuclei to produce endosperm is necessary for seed viability. Obligate apomicts are believed to have a completely closed recombination system; that is, recombination occurs only during microsporogenesis and is absent during megasporogenesis. In facultative apomicts, both apomictic and sexual modes of reproduction coexist.

The aforementioned types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. In addition, apomixis can increase the reproductive capacity of plants with distorted or adverse chromosome constitutions.

Apomixis can make hybrid development more efficient by eliminating the need for multiple crosses. It also simplifies hybrid production and increases genetic diversity in plant species with good male sterility systems. It would be ideal to find genes controlling obligate or a high level of apomixis in the cultivated species and be able to readily hybridize cross-compatible sexual x apomictic genotypes to produce true-breeding $F_1$ hybrids.

Soybean, Glycine max (L), is a valuable field crop. Thus, a continuing goal of plant breeders is to develop stable, high yielding soybean varieties that are agronomically sound. The reasons for this goal are to maximize the amount of grain produced on the land used and to supply food for both animals and humans. To accomplish this goal, the soybean breeder must select and develop soybean plants that have the traits that result in superior varieties. Current known varieties of soybeans show a percent conversion of less than 50% for conversion of flowers to pods and usually about 50 pods per plant.

Therefore it would be desirable to have a variety of soybeans that have a higher percent conversion and a greater number of pods per plant. It would further be desirable if there were a facile method for producing such a variety.

SUMMARY OF THE INVENTION

In one aspect of the present invention there is provided a method of producing a soybean apomictic plant that exhibits a greater percent conversion and a greater number of pods per plant comprising the steps of selecting a plurality of double ovule seeds; growing said seeds into soybean plants; selecting plants having a percent conversion greater than about 60% and at least 100 pods per plant.

In another aspect of the present invention there is provided further steps to the method of producing a soybean apomictic plant that exhibits an increased hybrid vigor compared to the parent plant comprising cross-breeding the selected apomictic soybean plant as a male with a different soybean plant as the female; selecting a plurality of seeds from the female soybean plant; growing said second seeds into soybean plants; selecting plants having a hybrid vigor of greater than about 50% and at least 100 pods per plant.

In a further aspect of the present invention there is provided apomictic soybean plants of variety S-201, CN-0629 and 7B1. Also provided are the seeds and progeny of these varieties.

In yet another aspect of the present invention there is provided a method of producing soybean seed, comprising crossing a plant of soybean variety S-201 with itself or a second soybean plant, representative seed of said soybean variety having been deposited under ATCC Accession No. PTA-11892 on May 24, 2011.

In a further aspect of the present invention there is provided a method of producing a plant of soybean variety S-201 comprising an added desired trait, the method comprising introducing a transgene conferring the desired trait into a plant of soybean variety S-201, representative seed of said soybean variety having been deposited under ATCC Accession No. PTA-11892 on May 24, 2011.

In another aspect of the present invention there is provided method of producing an inbred soybean plant derived from the soybean variety S-201, the method comprising the steps of preparing a progeny plant derived from soybean variety S-201 by crossing a plant of the soybean variety S-201 with a soybean plant of a second variety, representative seed of said soybean variety having been deposited under ATCC Accession No. PTA-11892 on May 24, 2011; crossing the progeny plant with itself or a second plant to produce a seed of a progeny plant of a subsequent generation; growing a progeny plant of a subsequent generation from said seed and crossing the progeny plant of a subsequent generation with itself or a second plant; and repeating the last two steps until an inbred soybean plant derived from the soybean variety S-201 is produced.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention is directed toward apomictic soybean varieties, including both plants and seeds. The apomictic soybean plants of the present invention have a percent conversion of flowers to pods of greater than about 60% and at least 100 pods per plant under normal growing conditions. It will be appreciated by those skilled in the art that these are typical values and may vary due to environmental parameters beyond the control of the skilled artisan. Also provided is a method for producing the apomictic soybean varieties of the present invention where characteristics of any variety can be stabilized through the use of apomixis. The seeds are grown and the resulting plants are selected for the desired traits including higher yield through a higher percent conversion of flowers to pods of greater than about 60% and at least 100 pods per plant.

Typical soybean plants and seeds currently being grown have a percent conversion of no greater than 50% for conversion of flowers to pods. A typical soybean plant has about 100 flowers and therefore will have no more than about 50 pods per plant. This limits the amount of soybeans currently produced per acre. The apomictic soybean varieties of the present invention have at least 100 pods per plant and often more than 300 pods per plant. Moreover, production of the soybean varieties of the present invention are produced in a shorter time frame because of the apomixes in one parent of the hybrid cross than normal breeding used to produce new varieties. The apomictic soybean varieties of the present invention meet the desire to increase the yield of soybeans per acre from current levels through the use of hybrid vigor.

Figure 1:
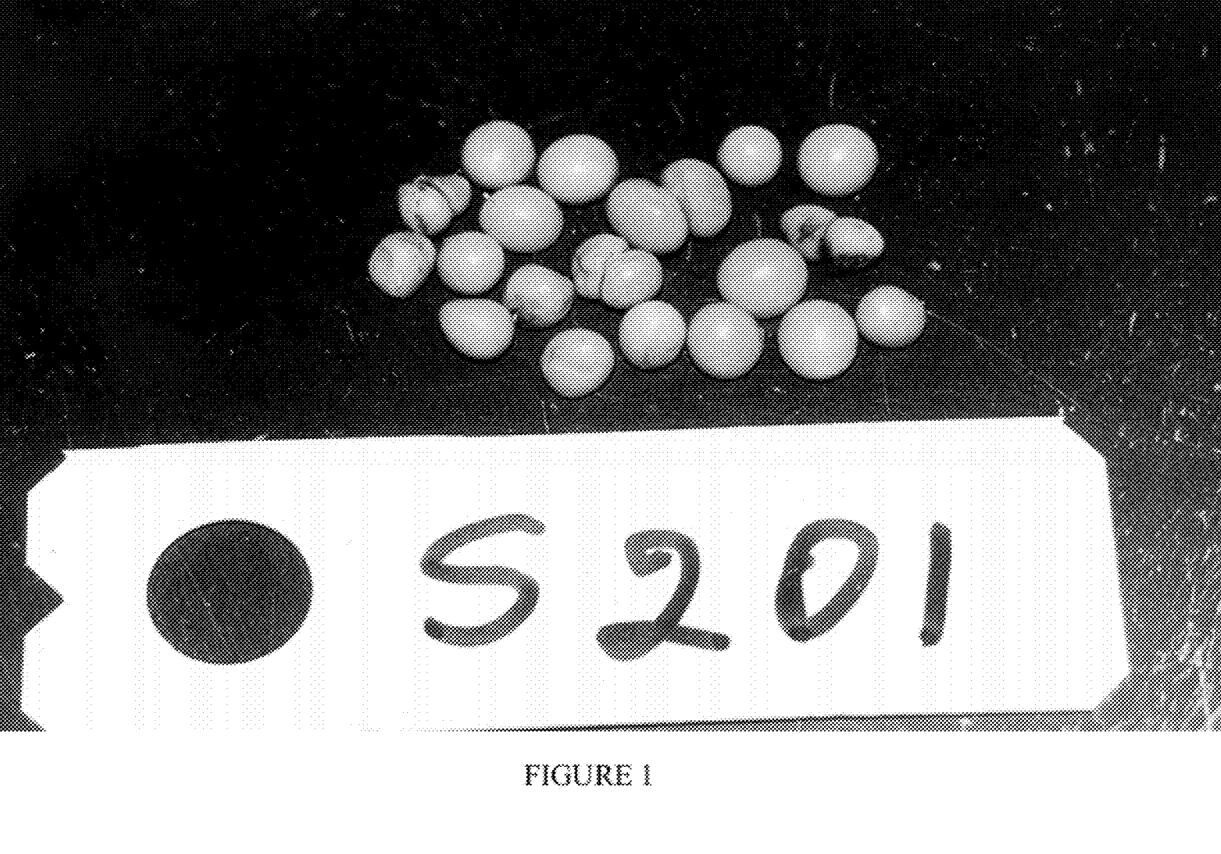
FIG. 1 is a photograph showing an example of selected double ovule seeds from soybean variety S-201.
Figure 2:
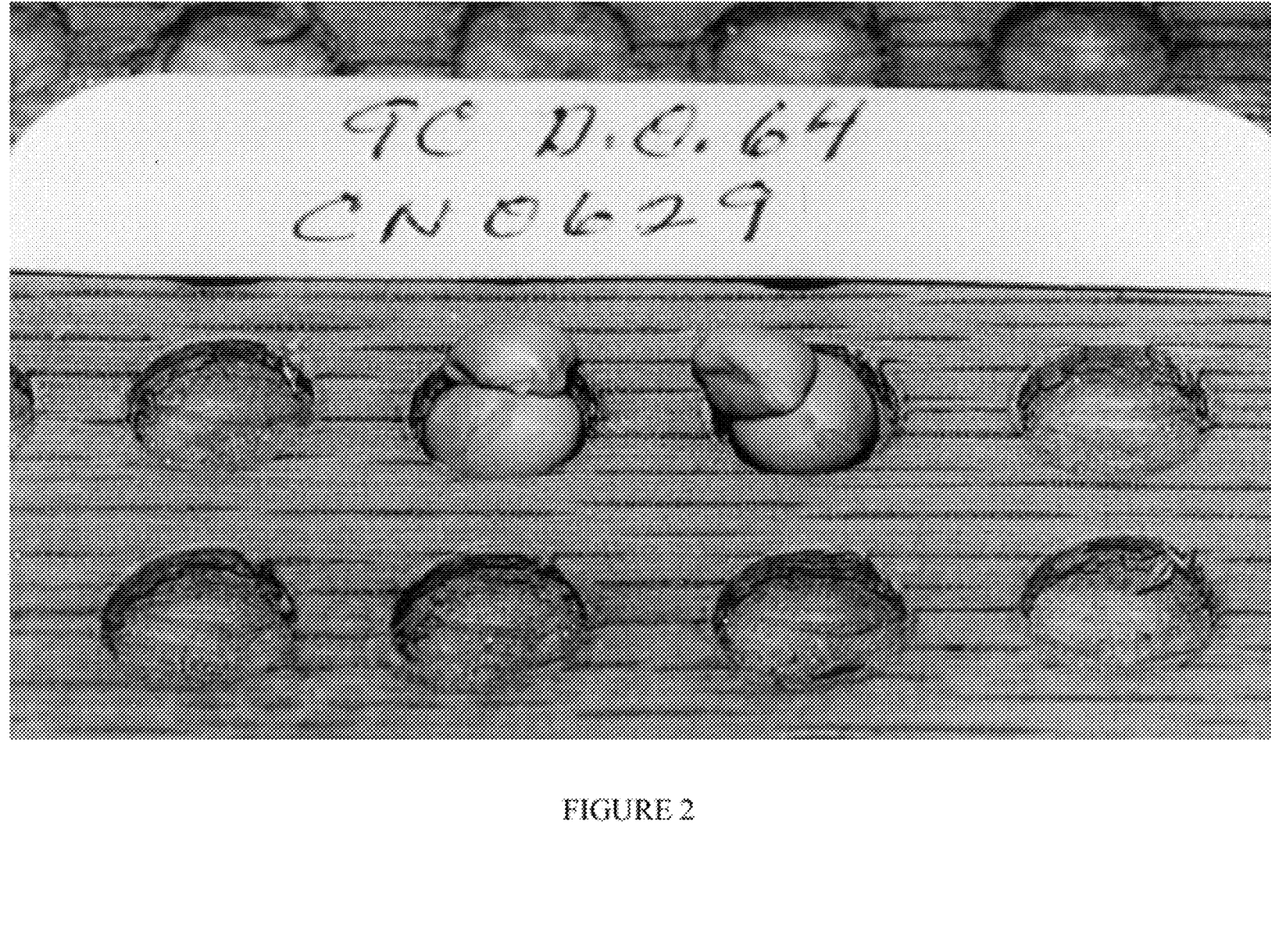
FIG. 2 is a photograph showing an example of a pair of end-to-end double ovule seeds from soybean variety CN-0629.
Figure 3:
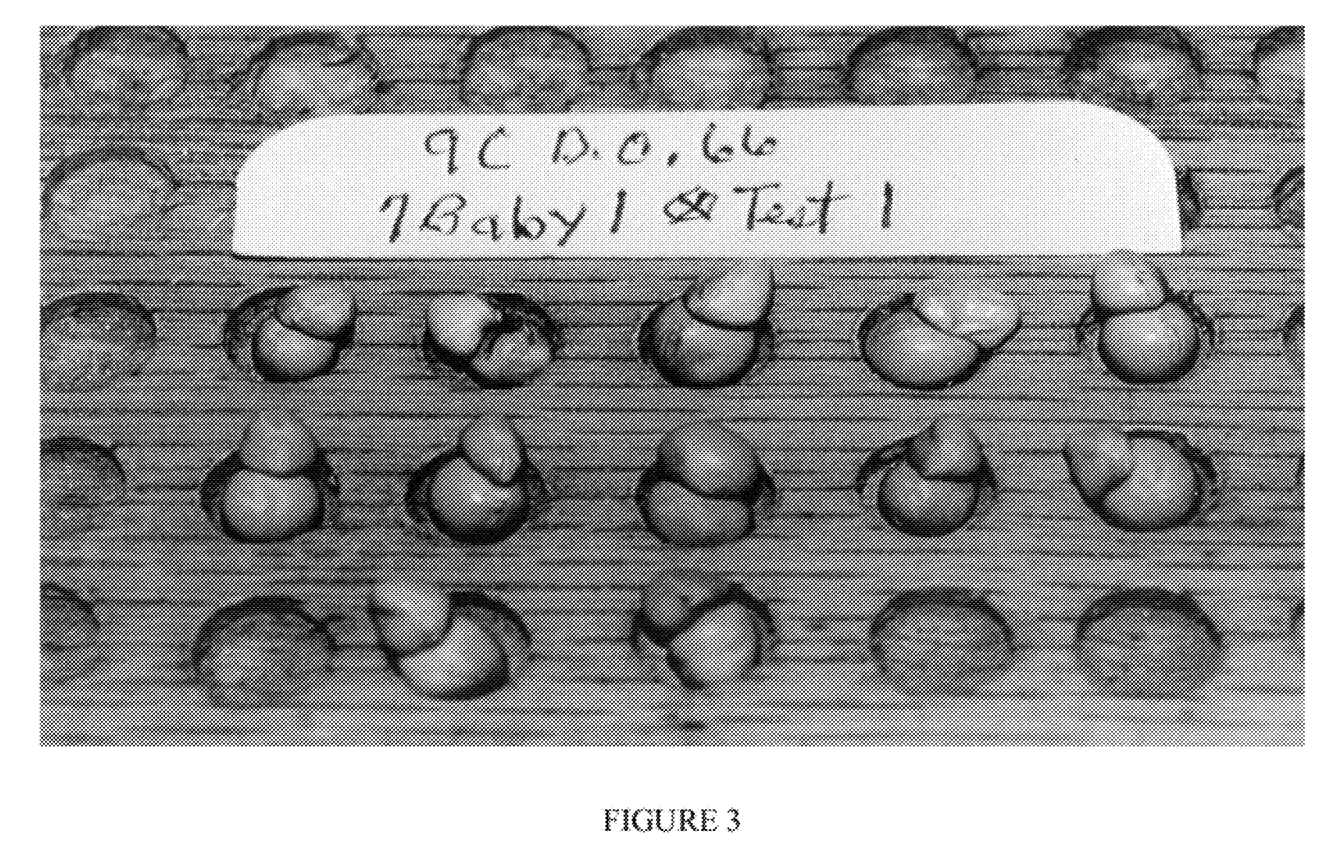
FIG. 3 is a photograph showing an example of end-to-end and side-to-side double ovules from soybean variety 7B1.

In one embodiment of the present invention there is provided a method for producing apomictic soybean varieties having a higher percent conversion of flowers to pods and a greater number of pods overall as compared to current varieties of soybean. The method comprises the steps of selecting double ovule seeds from seed lots of sources with desired traits of soybean germplasm. The number of seeds required can vary depending upon the viability of both ovules of the seed. In an illustrative embodiment the number of double ovule seeds required for economic development purposes may be from about 10,000 to 30,000. However, it will be appreciated that method of the present invention is not limited to the number of double ovule seeds initially selected. Examples of double ovule seeds are shown in FIGS. 1-3 for three different varieties of apomictic soybeans of the present invention. The double ovule seeds may be end to end or side to side. It has not been observed to make a difference as to the orientation of the double ovules.

In the next step, the seeds are grown out and observed for the percent conversion of flowers to pods and the total number of pods per plant. Lines with higher-than-normal numbers for these traits are selected to be used to produce the apomictic plants of the present invention. For example, plants may be selected having a percent conversion of greater than about 60%. In an illustrative embodiment, plants may be selected having a percent conversion greater than about 80% or even 90%. Additionally, the number of pods per plant may be greater than about 100, 200 or even 300. Plants have been produced by the method of the present invention having over 400 pods per plant. The plants may be also be tested for apomixis.

Figure 4:
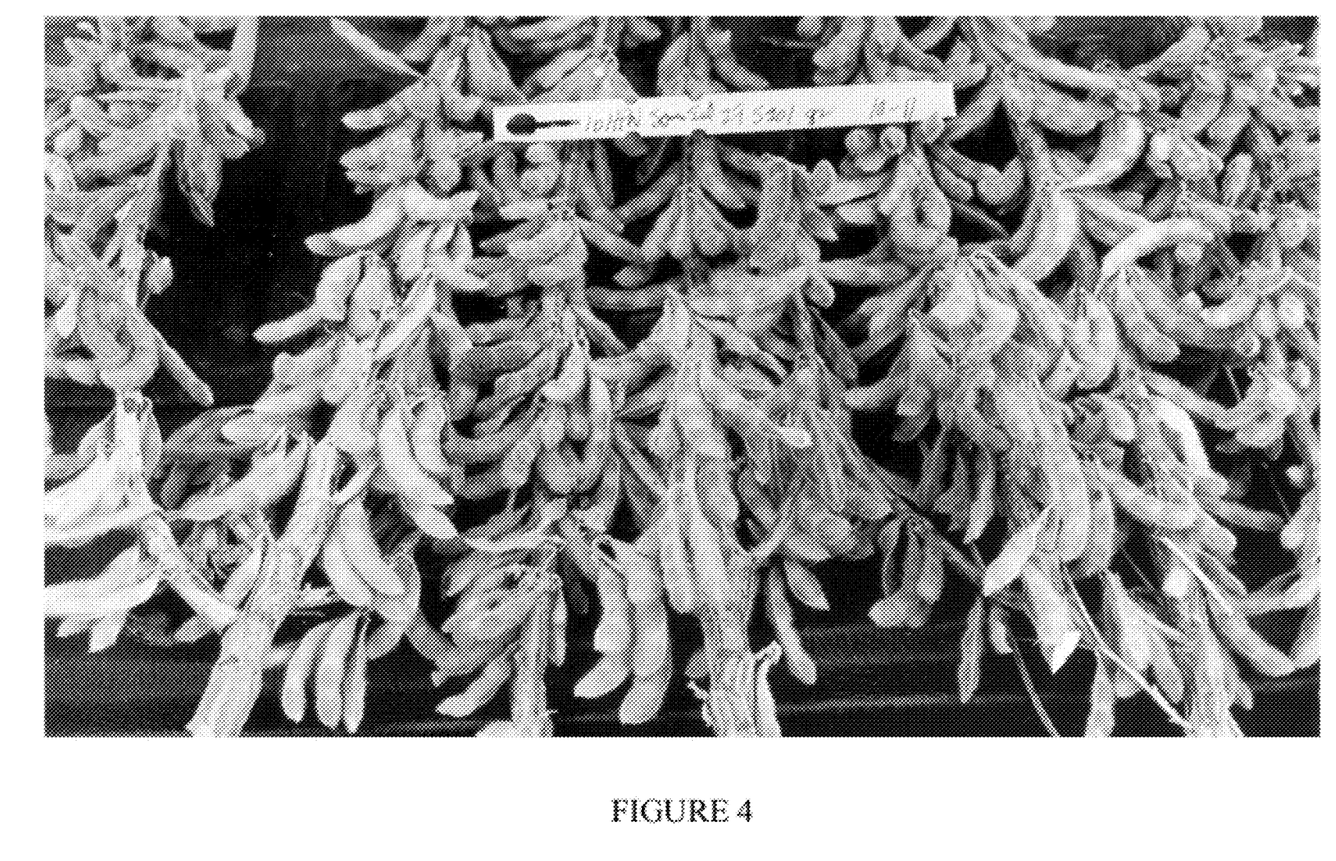
FIG. 4 is a photograph showing the uniformity of several soybean plants of soybean variety S-201 grown for selection.
Figure 5:
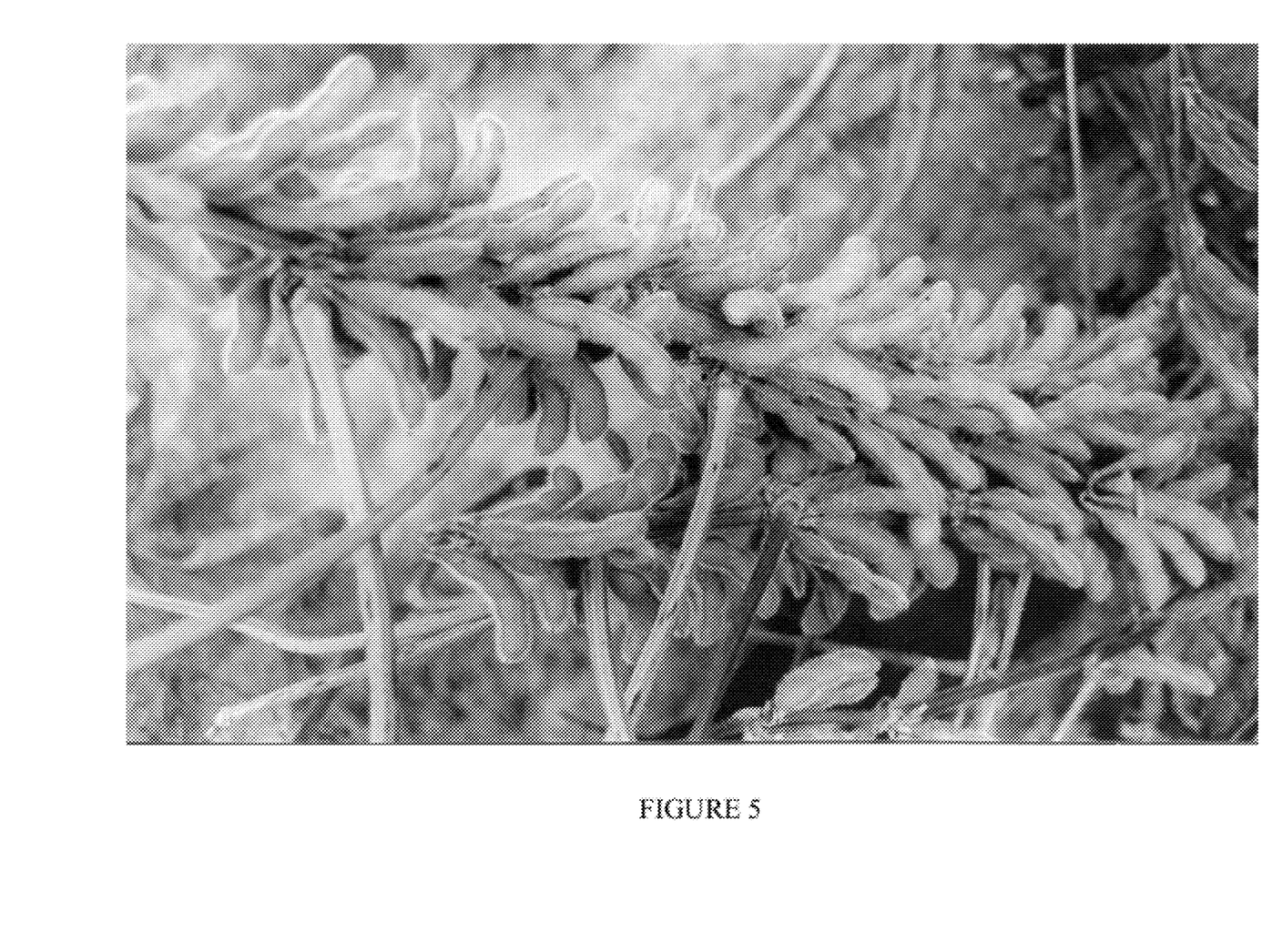
FIG. 5 is a photograph showing the typical percent conversion for an apomictic soybean variety according to the present invention.
Figure 6:
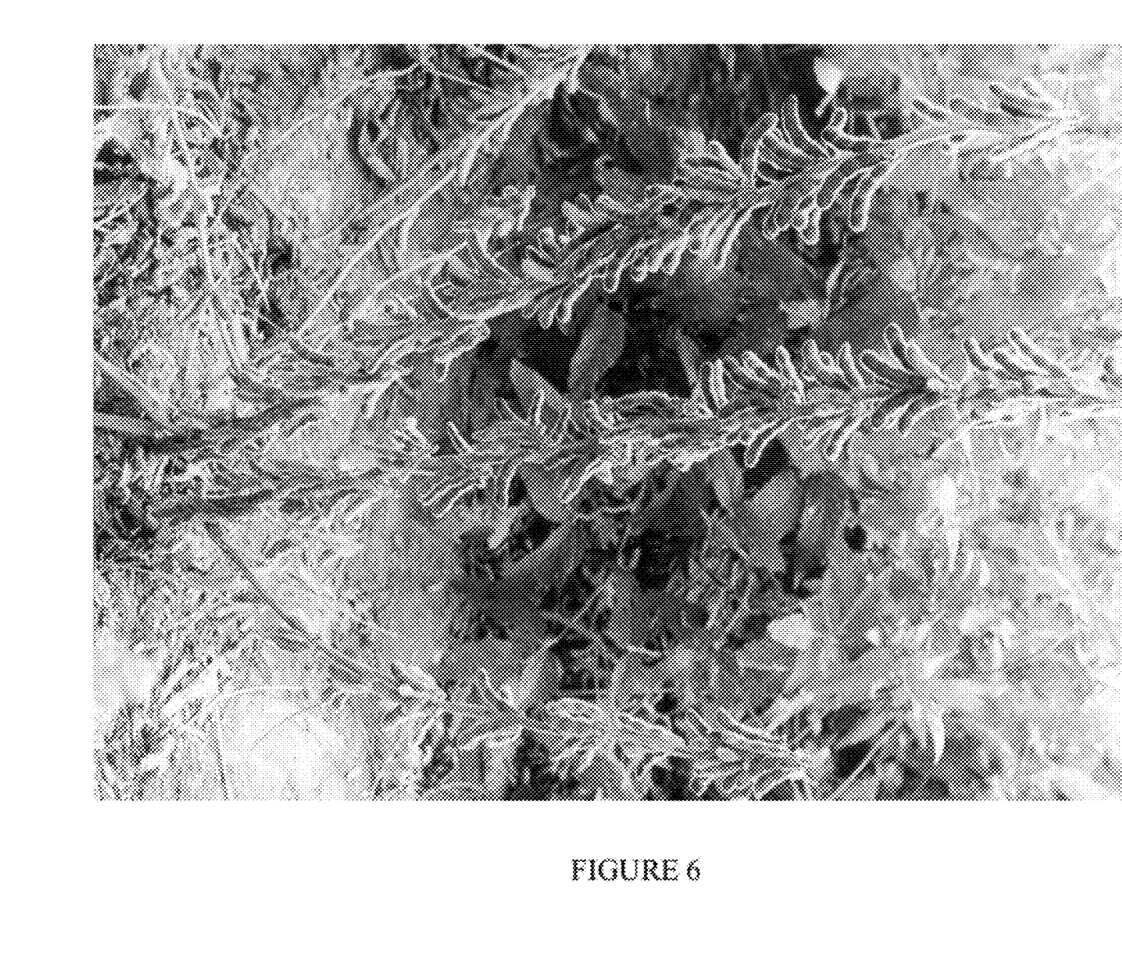
FIG. 6 is a photograph showing two 7B1 plants with more than 150 pods per plant.
Figure 7:
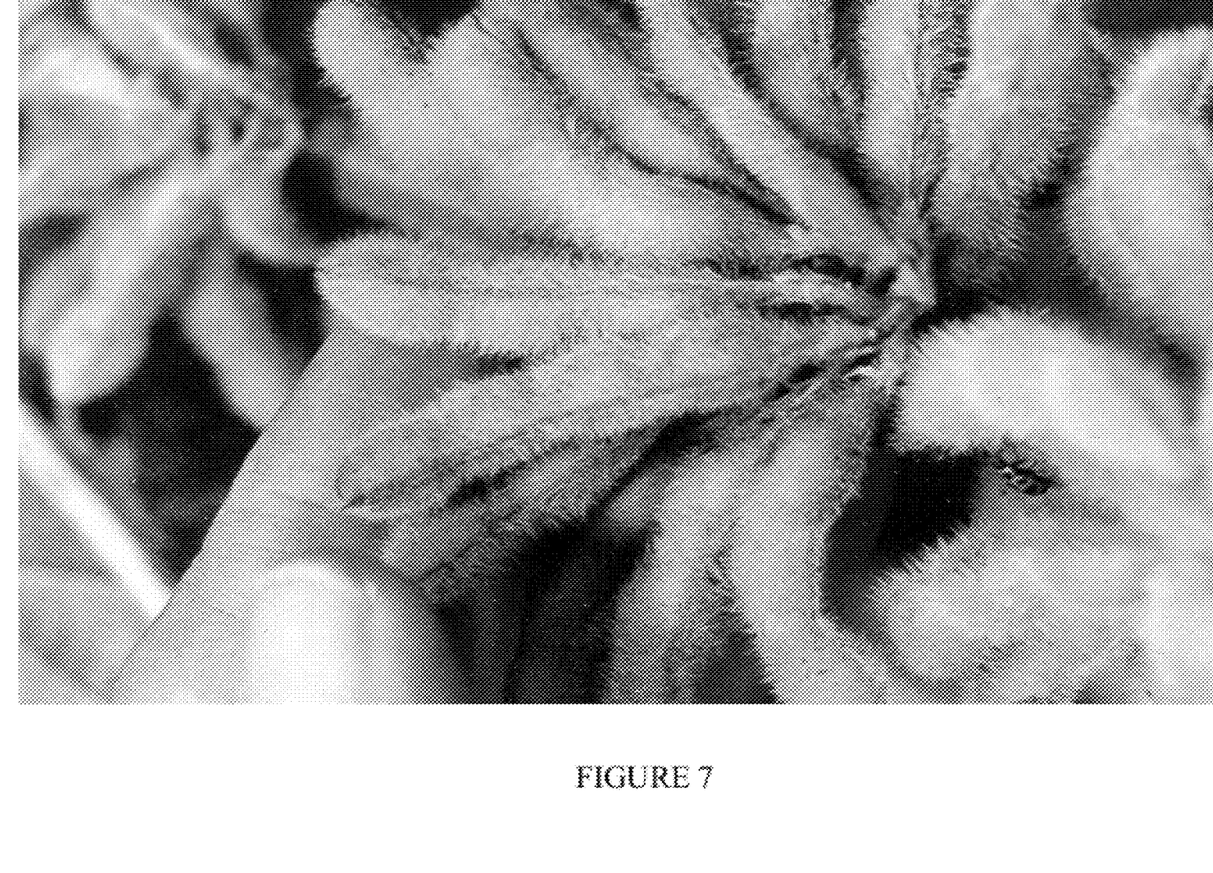
FIG. 7 is a photograph showing a single node of a 7B1 plant having 16 pods.
Figure 8:
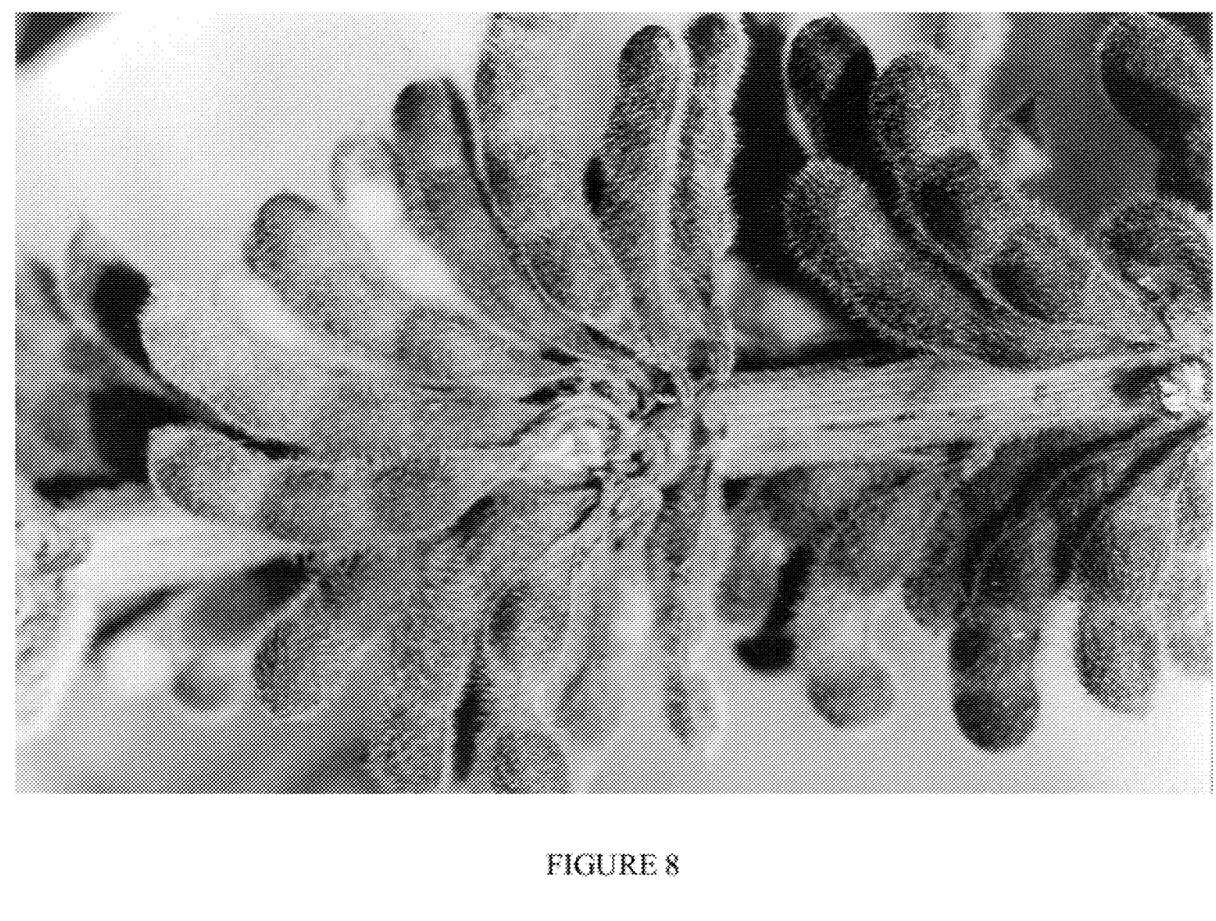
FIG. 8 is a photograph showing a single node of a 7B1 plant having a high percent conversion of flowers to pods.
Figure 9:
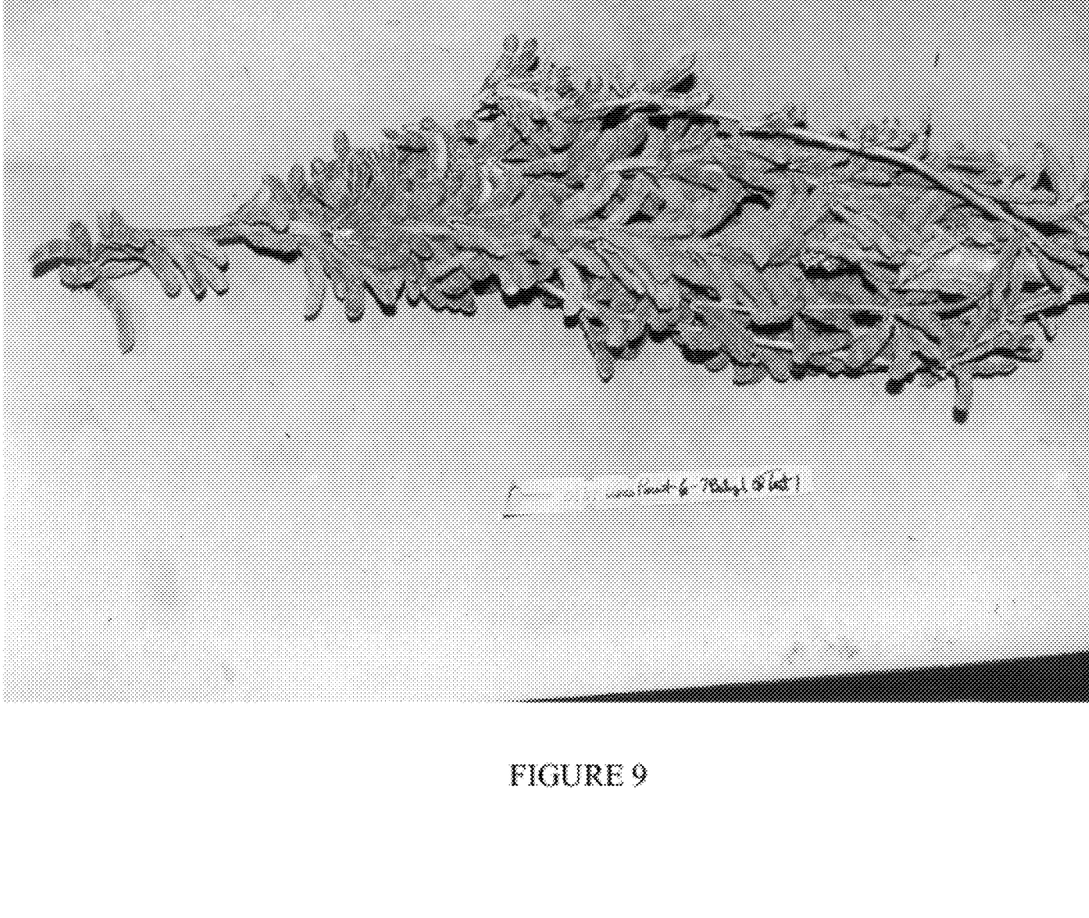
FIG. 9 is a photograph of the 7B1 plant of the line shown in FIGS. 6, 7 and 8.
Figure 10:
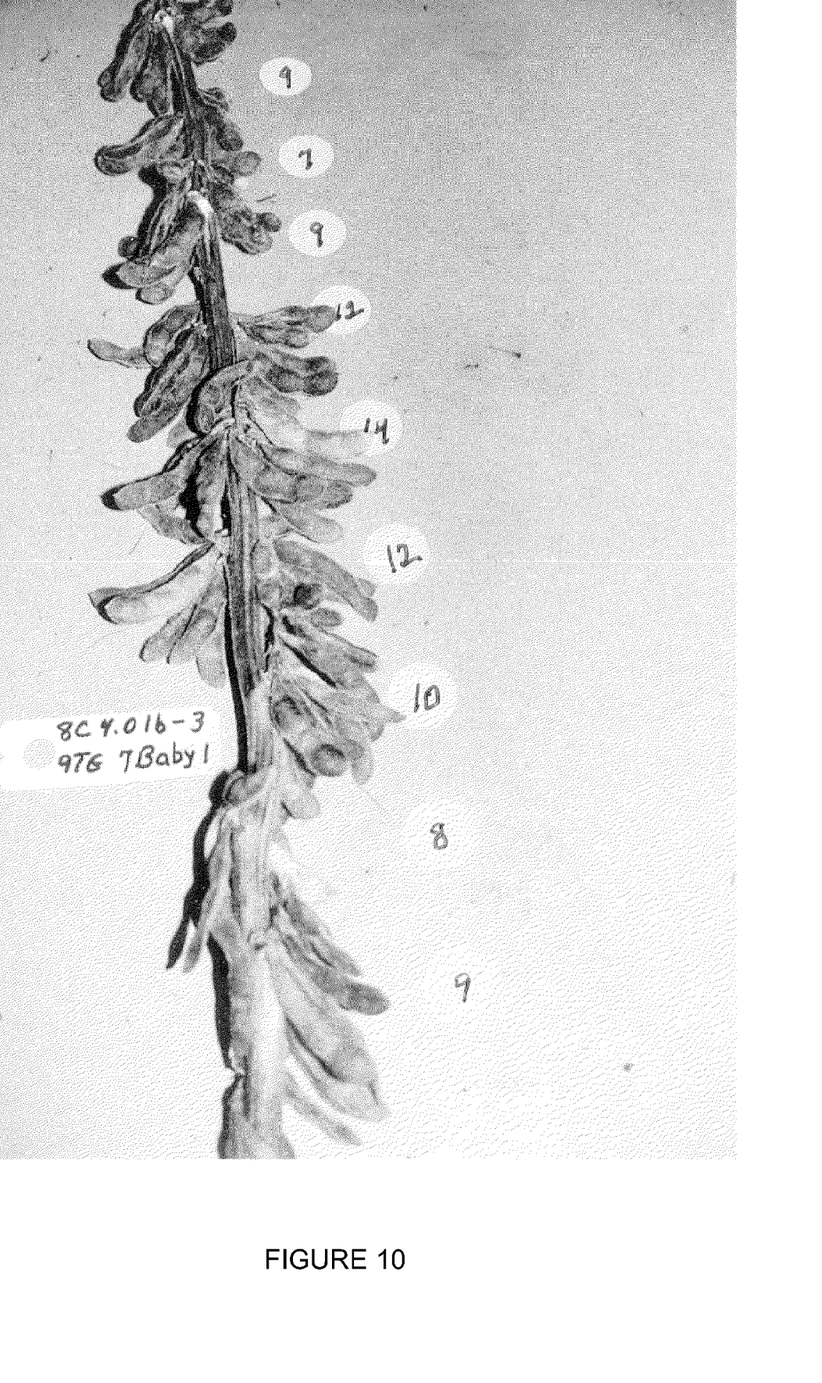
FIG. 10 is a photograph showing 90 pods on 9 nodes of a 7B1 plant.
Figure 11:
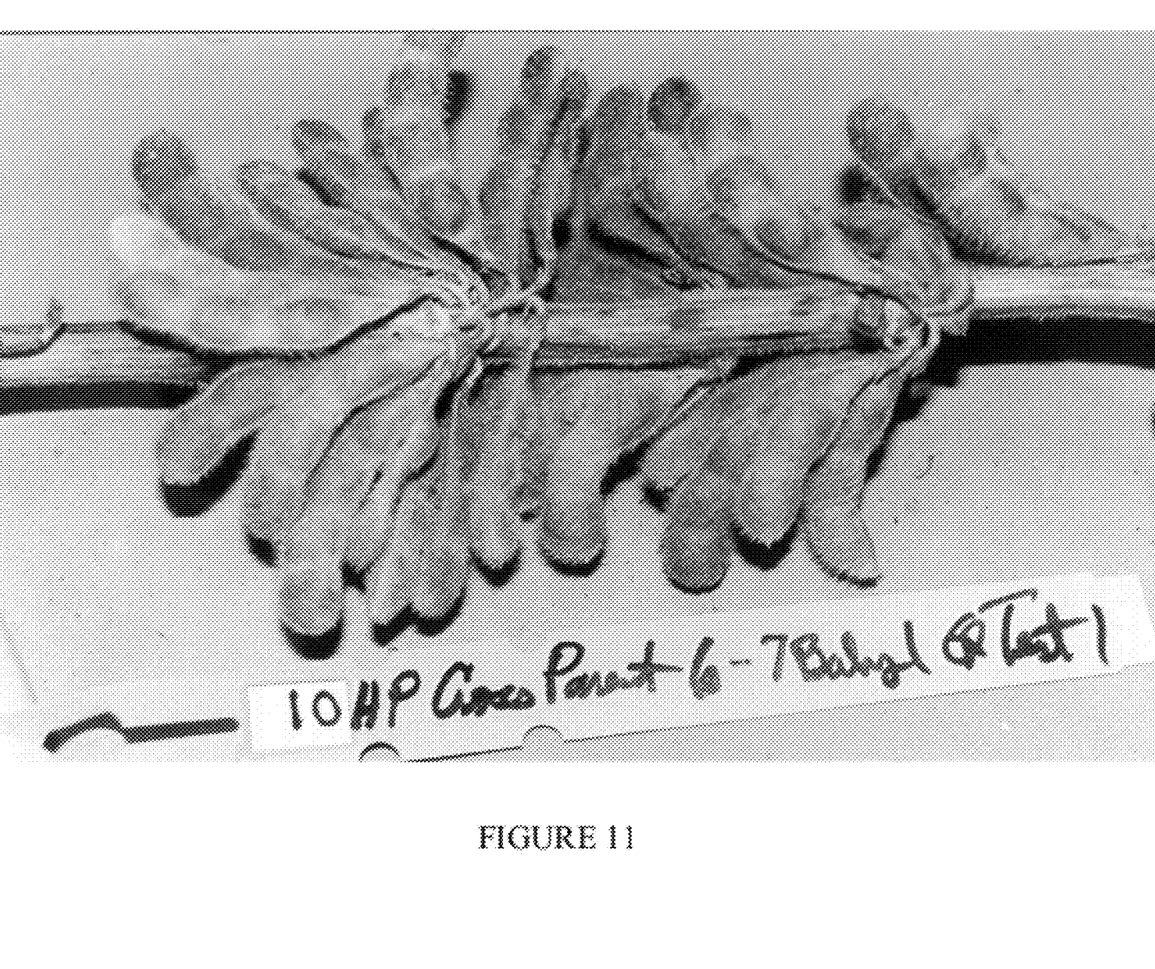
FIG. 11 is a photograph showing 38 pods on 3 nodes of a 7B1 plant.

FIG. 4 shows an example of one of the varieties produced by this method. S201 had a percent conversion of flower to pod approaching 100%. S-201 also produced a higher than normal amount of double ovule seeds having approximately 1.3 double ovule seeds per thousand seeds overall. This is about 10-fold greater than the current soybean seeds where the likelihood of a double ovule seed may be about 1 in 10,000. Double-ovule seeds from selected plants were grown the following year and emasculation was performed on 10 plants selected at random, indicated as variety 7B1 (FIGS. 6-11). All the pollen was removed from 10 flowers on each of the plants and tags indicated where each emasculated flower was located. Only one plant out of the 10 had no pods produced after emasculation. Apomixis occurs when an ovule begins dividing producing seed without the pollination that is normally required. It was concluded that the seed produced after the flowers were emasculated was due to apomixis. No pollen should have been available to the flowers on the selected plants because the anthers were removed long before the pollen was mature. The plants grown from the first pods produced on those plants have continued as apomictic single varieties for at least three years with significant uniformity observed in the plants each year. In addition, three of the ten original plants have produced progeny that had at least one double ovule.

In another embodiment of the present invention, the method may further comprise the steps of crossbreeding selected plants of soybean variety S-201 or its progeny with another soybean variety with desired traits. In an illustrative example, the plants of soybean variety S-201 or its progeny are used as male plants and the additional varieties are used as female plants. The seeds from the female plants are then harvested and grown. Plants are then selected for the desired traits as described above. This step may be repeated as many times as desired to obtain soybean plants with the added desired traits. The added desired traits may be, but not limited to, male sterility, herbicide tolerance, insect or pest resistance, disease resistance, modified fatty acid metabolism, modified carbohydrate metabolism and modified soybean fiber characteristics. In an alternate example the added trait may be herbicide tolerance where the tolerance is conferred to an herbicide such as, but not limited to, glyphosate, sulfonylurea, imidazalinone, dicamba, glufosinate, phosphinothricin, phenoxy proprionic acid, cycloshexone, triazine, benzonitrile and broxynil. (See U.S. Pat. Nos. 7,868,231, 7,868,232 and 7,572,958, all herein incorporated by reference in the entirety.)

In an alternate environment, desired traits may be conferred to the plants of soybean variety S-201 and/or its progeny by other methods such as recombinant techniques. Such methods are well known in the art.

Another apomictic variety of soybean selected from the $F_4$ the progeny of S-201 and labeled CN-0629. This variety was subsequently used to derive new lines, many which have produced more than 400 pods per plant. In crossbreeding of the CN-0629 variety, 61 different lines were used as females in crosses involving selected progeny from CN-0629 as males. The $F_1$ generation from this crossbreeding showed considerable variation in percent conversion and the number of pods. Most of the $F_1$ generation showed a phenotypic similarity when grown a year later. One such progeny was the variety 7B1 shown in FIGS. 5-11. The Figures show the increased number of pods per plant, particularly at each individual node.

Another characteristic of the apomictic soybean variety S-201 and its progeny is that they have determinate growth characteristics. The initial double ovule seeds were selected from a cross between an indeterminate soybean variety and a determinate variety that showed determinate characteristics. Nearly all soybean varieties exhibit one of two possible growth habits. Most indeterminate varieties are adapted to maturity group IV and earlier. These varieties are usually grown in the northern part of the country. These varieties have overlapping vegetative and reproductive growth periods. Usually less than one-half of the main stem nodes have developed when flowering begins. Stem growth continues as flowering progresses up the stem. Indeterminate stems do not end with a terminal raceme or the raceme is much reduced in size. Flowers and pods develop at different times and rates depending on node locations. Nodes with the earliest flowers and slowest developing pods are located near the bottom of the stem.

Most varieties with a determinate growth habit are adapted to maturity group V and later than Group IV. These varieties are normally grown in the southern part of the country and do not grow well further north. These varieties have rather distinct vegetative and reproductive development periods. Few stem nodes develop once flowering begins and the stem ends with a terminal raceme. Flowers and pods tend to develop at about the same time and rate for all stem nodes. A few varieties with determinate growth habit have been released for northern soybean production areas. These varieties are usually classified as semi-dwarf and obtain about one-half to two-thirds the height of other adapted varieties.

A unique characteristic of the apomictic soybean varieties of the present invention is that they have determinate growth habits and have stems with a terminal raceme. However, unlike the usual soybeans with determinate growth habits, the soybean varieties of the present invention show a hardiness that allows them to grow in the northern part of the country. Moreover, in contrast to both usual varieties with either determinate or indeterminate growth characteristics, the soybean varieties of the present invention have a higher percent conversion of flowers to pods and a greater number of pods per plants.

A deposit of the soybean variety S-201, which is disclosed herein above and referenced in the claims, was made with the American Type Culture Collection (ATCC), 10801 University Blvd., Manassas, Va. 20110-2209. The date of deposit is May 24, 2011, and the accession number for those deposited seeds of soybean variety S-201 is ATCC Accession No. PTA-11892. The deposit is intended to meet all of the requirements of 37 C.F.R. section 1.801-1.809. The deposit will be maintained in the depository for a period of 30 years, or 5 years after the last request, or for the effective life of the patent, whichever is longer, and will be replaced if necessary during that period.

It should be understood, of course, that the foregoing relates to exemplary embodiments of the invention and that modifications may be made without departing from the spirit and scope of the invention as set forth in the following claims.

I claim:

1. A seed of soybean variety S-201, representative seed of said soybean variety having been deposited under ATCC Accession No. PTA-11892.

2. A method of producing soybean seed, comprising crossing a plant of soybean variety S-201 with itself or a second soybean plant, representative seed of said soybean variety having been deposited under ATCC Accession No. PTA-11892.

3. The method of claim 2, further defined as a method of preparing hybrid soybean seed, comprising crossing a plant of soybean variety S-201 with a second, distinct soybean plant, representative seed of said soybean variety S-201 having been deposited under ATCC Accession No. PTA-11892.

4. An $F_1$ hybrid seed produced by the method of claim 3.

5. A method of producing a plant of soybean variety S-201 comprising an added desired trait, the method comprising introducing a transgene conferring the desired trait into a plant of soybean variety S-201, wherein the plant comprises the transgene and otherwise all of the physiological and morphological characteristics of soybean variety S-201, representative seed of said soybean variety having been deposited under ATCC Accession No. PTA-11892.

6. The method of claim 5, wherein the desired trait is selected from the group consisting of male sterility, herbicide tolerance, insect or pest resistance, disease resistance, modified fatty acid metabolism, modified carbohydrate metabolism and modified soybean fiber characteristics.

7. The method of claim 5, wherein the desired trait is herbicide tolerance and the tolerance is conferred to an herbicide selected from the group consisting of glyphosate, sulfonylurea, imidazalinone, dicamba, glufosinate, phosphinothricin, phenoxy proprionic acid, cycloshexone, triazine, benzonitrile and broxynil.

8. A plant produced by the method of claim 5.

9. A plant of soybean variety S-201 grown from the seed of claim 1.

10. A plant part of the plant of claim 9.

11. The plant part of claim 10 wherein the part is selected from the group consisting of pollen grain, ovule, protoplast, cell, embryo, cotyledon, hypocotyl, meristem, root, pistil, anther, flower, stem, pod, leaf, and petiole.

12. $F_1$ progeny of the soybean variety S-201 of claim 9.

13. $F_1$ progeny of the soybean plant of claim 9 wherein an added desired trait has been introduced into the plant of claim 9, wherein the plant comprises the desired trait and otherwise all of the physiological and morphological characteristics of soybean variety S-201, representative seed of said soybean variety having been deposited under ATCC Accession No. PTA-11892.

14. The $F_1$ progeny of claim 13, wherein the desired trait is herbicide tolerance and the tolerance is conferred to an herbicide selected from the group consisting of glyphosate, sulfonylurea, imidazalinone, dicamba, glufosinate, phosphinothricin, phenoxy proprionic acid, cycloshexone, triazine, benzonitrile and broxynil.

15. A method of producing soybean seed, said method comprising planting seed of soybean variety S-201, wherein a representative sample of seed of soybean variety S-201 has been deposited under ATCC Accession No. PTA-11892 until seed is produced, and collecting the seed.

16. A method of producing a soybean plant derived from soybean variety S-201, said method comprising crossing the plant of claim 9 with a second soybean plant to produce a progeny soybean plant derived from soybean variety S-201.

17. A plant produced by the method of claim 16, wherein the second soybean plant is also a plant of soybean variety S-201, or wherein the plant derived from soybean variety S-201 is an $F_1$ progeny.

18. A method of producing a commodity plant product, comprising obtaining the plant of claim 9 or a part thereof and producing said commodity plant product therefrom.

19. The method of claim 18, wherein the commodity plant product is protein concentrate, protein isolate, hulls, meal, flour, or oil.

20. A soybean variety S-201 plant, representative seed of said soybean variety having been deposited under ATCC Accession No. PTA-11892, wherein the variety has a flower to pod percent conversion greater than 60% and less than 100%, and greater than 100 and up to 400 pods per plant.

* * * * *